(12) United States Patent
Morita et al.

(10) Patent No.: US 6,958,227 B2
(45) Date of Patent: Oct. 25, 2005

(54) CELLULOSE PRODUCED BY FILAMENTOUS FUNGI

(75) Inventors: Naoki Morita, Hokkaido (JP); Tamotsu Hoshino, Hokkaido (JP); Michiko Sawada, Hokkaido (JP); Hidetoshi Okuyama, Hokkaido (JP); Midori Kuriki, Hokkaido (JP); Akira Kawakami, Hokkaido (JP); Fumihiro Terami, Hokkaido (JP)

(73) Assignee: Incorporated Administrative Agency National Agriculture and Bio-Oriented Research Organization, Ibaraki (JP)

( * ) Notice: Subject to any disclaimer, the term of this patent is extended or adjusted under 35 U.S.C. 154(b) by 76 days.

(21) Appl. No.: 10/369,327

(22) Filed: Feb. 14, 2003

(65) Prior Publication Data

US 2003/0170830 A1 Sep. 11, 2003

Related U.S. Application Data

(63) Continuation of application No. 09/676,054, filed on Sep. 29, 2000, now abandoned.

(30) Foreign Application Priority Data

Oct. 1, 1999  (JP) ............................................ 11-281425
Sep. 11, 2000  (JP) ...................................... 2000-275211

(51) Int. Cl.[7] ............................ C12P 19/04; C12N 1/14; C08B 1/00
(52) U.S. Cl. ....................... 435/101; 435/254.1; 536/56
(58) Field of Search ............................. 435/101, 254.1; 536/56

(56) References Cited

U.S. PATENT DOCUMENTS 6,168,799 B1 * 1/2001 Klein .......................... 424/401
6,329,192 B1 * 12/2001 Ben-Basaat et al. ........ 435/101

FOREIGN PATENT DOCUMENTS

WO    WO 99/24555    5/1999    ............ C12N/1/14

OTHER PUBLICATIONS

Aldrich Catalogue—Aldrich Chemical Comp, Inc Milwaukee, WIS 53233 Publ. 1988 p. 312 Cellulose.*
Database Chemabs Online!, Chemical Abstracts Service, Columbus, Ohio, US; Olesko, V.B. et al., "Carbohydrate composition of some filamentous fungi" retrieved from STN, Database accession No. 114:97891, XP002158710.
Database Chemabs Online!, Chemical Abstracts Service, Columbus, Ohio, US; Schweiger–Hufnagel, Ulride Et al., Identification of the extracellular polysaccharide produced by the snow mold fungus *Microdochium nivale*: retrieved from STN, Database accession No. 132:305555, XP002158711.
Akira Misaki, "Cell wall polysaccharides of Eumycetes (e.g., yeasts and fungi)", First Impression of the First Edition, Dec. 1, 1974 (English translation included).
Mikol Fitopatol, "Carbohydrate composition of some filamentous fungi", vol. 24, No. 5, p. 430–434, 1990 (English abstract).

* cited by examiner

Primary Examiner—Herbert J. Lilling
(74) Attorney, Agent, or Firm—Fish & Richardson P.C.

(57) ABSTRACT

The present invention relates to a method of producing cellulose comprising the steps of:

(i) culturing filamentous fungus having the ability to produce cellulose; and
(ii) recovering cellulose from a culture obtained by the step (i) and cellulose produced by filamentous fungi.

The present invention provides technology to produce cellulose from filamentous fungi. Further, the present invention provides novel cellulose, which is produced by filamentous fungi and can be utilized as various industrial materials, additives, and the like.

3 Claims, 6 Drawing Sheets

FIG.1
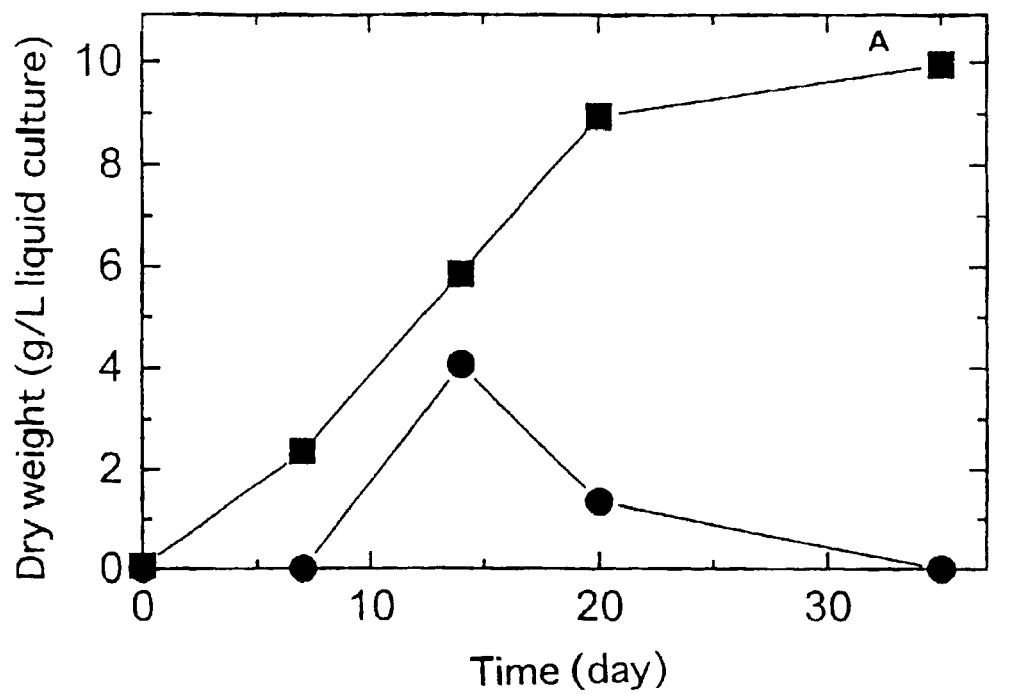
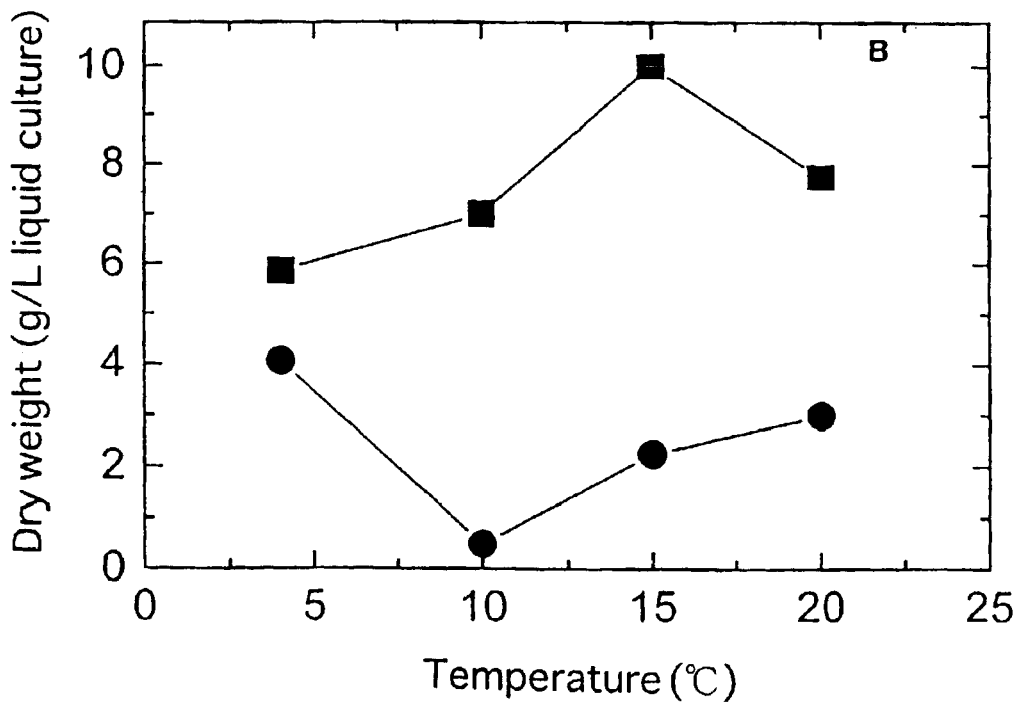

FIG.6
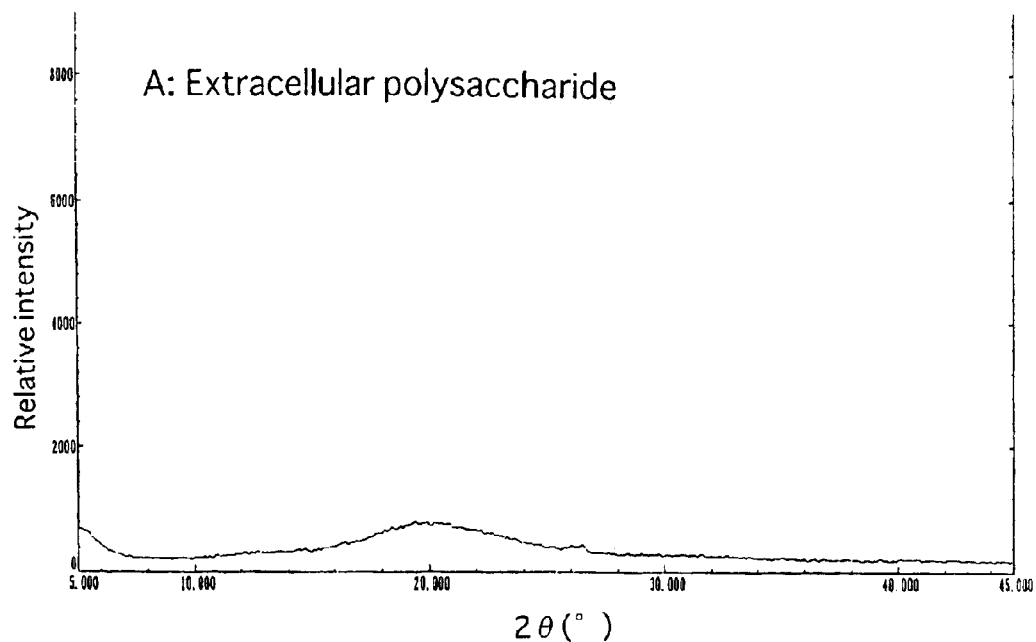
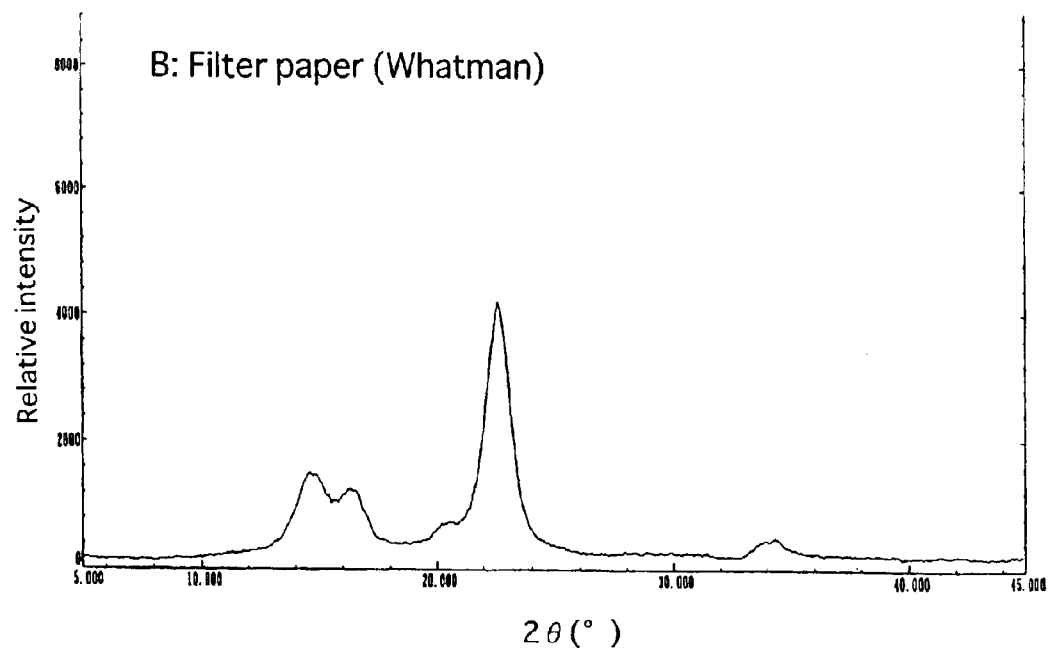

CELLULOSE PRODUCED BY FILAMENTOUS FUNGI

CROSS REFERENCE TO RELATED APPLICATIONS

This application is a continuation under 35 U.S.C. §120 of U.S. patent application Ser. No. 09/676,054, filed Sept. 29, 2000 now abandoned. The disclosure of the prior application is considered part of and incorporated by reference in the disclosure of this application.

FIELD OF THE INVENTION

The present invention relates to microbial production of cellulose, in particular, to a method of producing cellulose using cellulose-producing fungi belonging to psychrophilic filamentous fungi and cellulose obtained by this production method.

The strain *Microdochium nivale*, FERM: BP-7298, was originally deposited on Sept. 2, 1999. The deposit has been made under the terms of the Budapest Treaty and all restrictions imposed by the depositor on the availability to the public of the deposited material will be irrevocably removed upon the granting of a patent. The International Depositary Authority is the National Institute of Bioscience and Human-Technology Agency of Industrial Science and Technology. The address for the depository is 1–3, Higashi 1-chome, Tsukuba-shi, Ibaraki-ken 305-8566, JAPAN.

BACKGROUND OF THE INVENTION

Cellulose is a major constituent of the cell wall of plants. Most cellulose for use as paper is derived from plants, such as woods.

In addition to plants, some bacteria, prokaryotic organisms, produce extracellular cellulose, called bacterial cellulose, in the culture medium during cultivation. Because of its superior property of dispersing in water, the bacterial cellulose has been utilized as an additive for food and cosmetics. Since it has physical properties different from those of cellulose produced from a wood pulp and the like, it has been applied as various industrial materials, for example, to an acoustic oscillation board in an audio speaker.

On the other hand, filamentous fungi, which are eukaryotes, are known to produce extracellular polysaccharides. Among polysaccharides produced by such filamentous fungi, polysaccharides, which have been reported so far to consist of glucose, similar to cellulose, are α-glucan including pullulan and elsinan, and β-glucan including β- (1→3)-glucan with branches or side chains of β-(1→3)·(1→6)-glucan and β-(1→6)·β-(1→4) glucan.

It has not been reported that filamentous fungi produce cellulose which is β-(1→4)-glucan.

SUMMARY OF THE INVENTION

The object of this invention is to provide a method of producing cellulose using filamentous fungi and cellulose produced by the filamentous fungi.

As a result of diligent research to solve the above problems, the inventors have completed the invention by finding that *Microdochium nivale* belonging to psychrophilic filamentous fungus produces insoluble polysaccharide in a large quantity in the culture medium during cultivation of the organism, and produced polysaccharide is cellulose.

The present invention encompasses the following inventions.

(1) A method of producing cellulose comprising the steps of:
(i) culturing filamentous fungus having the ability to produce cellulose; and
(ii) recovering cellulose from a culture obtained by the step (i).
(2) The method of (1), wherein the filamentous fungus belongs to the genus Microdochium.
(3) The method of (1), wherein the filamentous fungus is *Microdochium nivale* (FERM BP-7298).
(4) Cellulose produced by filamentous fungus.
(5) The cellulose of (4), wherein the filamentous fungus belongs to the genus Microdochium.
(6) The cellulose of (4), wherein the filamentous fungus is *Microdochium nivale* (FERM BP-7298).
(7) Cellulose which is obtained by the method of (1).
(8) Cellulose which has the physico-chemical properties of:
(a) being completely hydrolyzed when it is treated in 2M trifluoroacetic acid for 2 hours at 121° C.; and (b) showing no peak at 2θ=5.0° to 45.0° when it is lyophilized (freeze-dried) and subjected to X-ray diffraction analysis.

This specification includes part or all of the contents as disclosed in the specification and/or drawings of Japanese Patent Application Nos.1999-281425 and 2000-275211, which is a priority document of the present application.

BRIEF DESCRIPTION OF THE DRAWINGS

FIG. 1 is a graph showing (A) Changes with time in the amount of extracellular insoluble polysaccharide produced by *Microdochium nivale* while culturing the organisms at 4° C., and (B) The relationship between the amount of extracellular insoluble polysaccharide produced from *Microdochium nivale* and the culture temperature. Symbols: ● indicates the amount of insoluble polysaccharides and ■ indicates the amount of *Microdochium nivale* cells.

FIG. 6 shows X-ray diffraction of (A) insoluble polysaccharide produced by *Microdochium nivale*, and (B) a filter paper (Whatman) (vegetable cellulose).

DESCRIPTION OF THE PREFERED EMBODIMENTS

Figure 2:
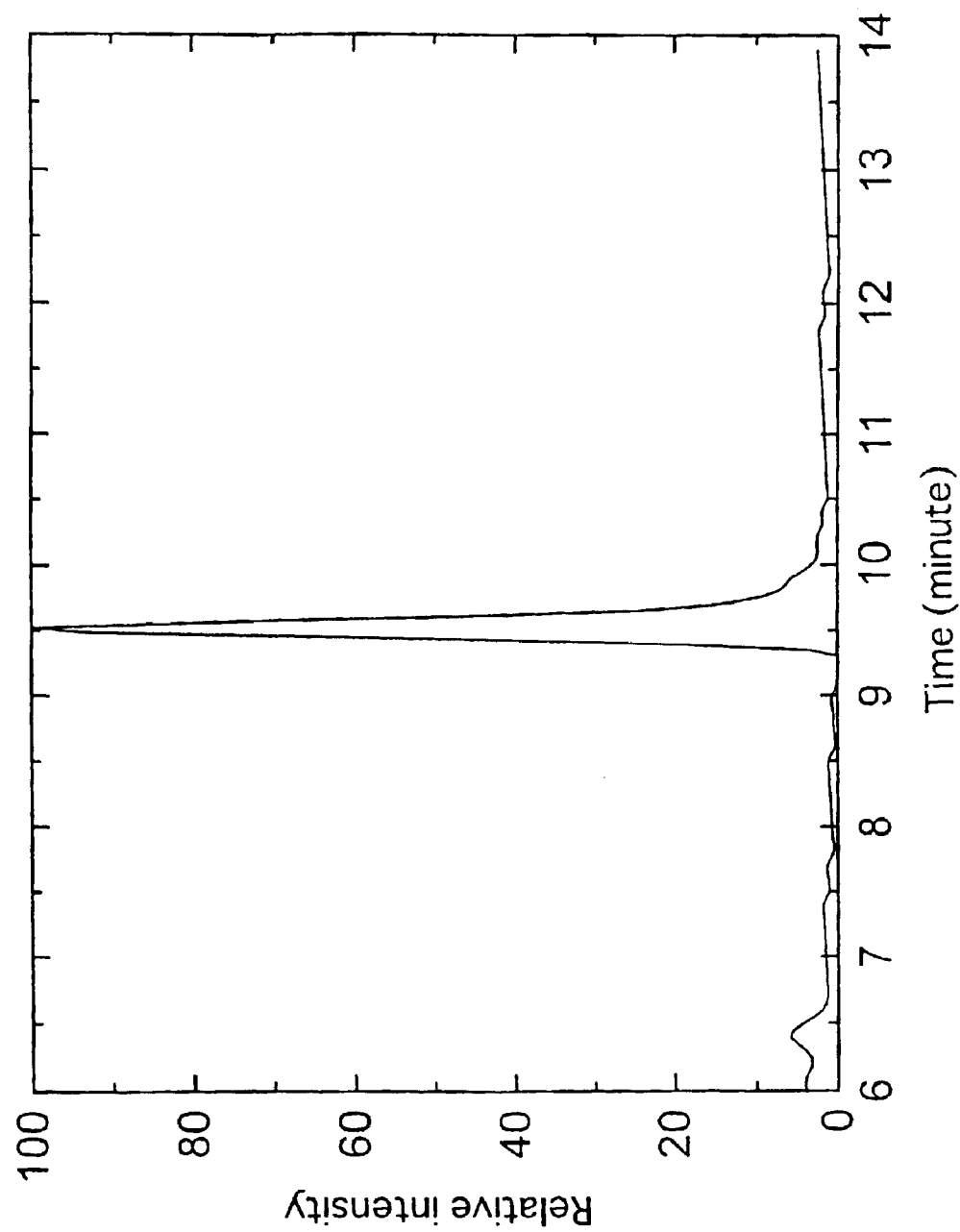
FIG. 2 shows the results of constituent sugar analysis by gas chromatography performed on insoluble polysaccharide produced by *Microdochium nivale*.

The present invention relates to cellulose produced by filamentous fungi. Filamentous fungi used herein may be any filamentous fungi having the ability to produce cellulose, without other limitation. Preferred examples of the filamentous fungi are, but are not limited to, those belonging to the genera Microdochium. A particularly preferred filamentous fungus is a snow mold, *Microdochium nivale*, which was deposited with National Institute of Bioscience and Human Technology, Agency of Industrial Science and Technology (1–3, Higashi 1-chome, Tsukuba-shi, Ibaraki-ken 305-0046, Japan) on Sep. 2, 1999 (Accession No. FERM BP-7298)

The present invention also relates to a method of producing cellulose comprising the steps of (i) culturing filamentous fungus having the ability to produce cellulose; and (ii) recovering cellulose from a culture obtained by step (i). The filamentous fungus used in this method is as described above. According to this method, cellulose of the invention can be properly produced.

Media used for culturing the filamentous fungus may be any media known to allow filamentous fungi to grow, without other limitation. Either liquid or solid media may be used. Preferably, a liquid medium is employed. A particularly preferred medium used in the invention is a liquid potato dextrose medium.

Culturing may be performed by any method known to those skilled in the art, including shaking culture, stationary culture, and the like. A preferred culturing method is shaking culture. In liquid culture, the amount of cells added to a medium is not specifically limited because it can be properly determined by those skilled in the art. The amount of cells to be added per 200 ml of a medium is preferably 0.01 g to 0.15 g, more preferably 0.04 g to 0.08 g.

When the amount of cells is represented by weight in this specification, unless otherwise specified, the cell amount is represented by the wet weight (weight of cells in wet conditions) which is obtained by centrifuging cultured cells to remove the supernatant fluid.

Further, in solid culture, the amount of cells added to a medium is not specifically limited because it can be properly determined by those skilled in the art.

Temperature for culturing is not specifically limited, because it can be determined based on the results of examinations for efficiency of cellulose production by filamentous fungi at various temperatures. When *Microdochium nivale* (FERM BP-7298) is used as filamentous fungus, culture temperature may be determined according to graph B in FIG. 1. Temperature for culturing is not specifically limited as described above. However in a temperature range below 10° C., a preferred temperature ranges from 2° C. to 8° C., more preferably 3° C. to 6° C., and the most preferably at about 4° C. In a temperature range above 10° C., a preferred temperature ranges from 12° C. to 25° C., more preferably 15° C. to 22° C., and the most preferably at about 20° C.

The culturing period is not specifically limited, because it can be determined based on the results of examinations for efficiency of cellulose production by filamentous fungi for various culturing periods. When *Microdochium nivale* (FERM BP-7298) is used as filamentous fungus and cultured at 4° C., a culturing period may be determined according to graph A in FIG. 1. As described above, the culturing period is not specifically limited. A preferred culturing period is from 7 to 35 days, more preferably 10 to 20 days, and the most preferably about 14 days.

According to the preferred embodiment of this invention, cellulose can be efficiently produced by inoculating and shake-culturing *Microdochium nivale* (FERM BP-7298) in a potato dextrose (2.4%) liquid medium (pH 5.1) for 14 days at 4° C. For example, when 0.06 g of *Microdochium nivale* is inoculated in 200 ml of the said liquid medium and cultured while turning the medium placed in a 500 ml flask at 200 rpm, 4 g/l of cellulose can be produced.

Thus produced intracellular or extracellular cellulose can be recovered by known methods. When cellulose is produced intracellularly, cellulose can be recovered by known methods from a mixture obtained from the disrupted cells. When cellulose is produced extracellularly, cellulose can be recovered by known methods from portions other than the cells in the culture. For example, cellulose produced in a liquid medium can be recovered by centrifuging the liquid medium to collect the fraction containing insoluble polysaccharide.

The recovered cellulose can be washed with distilled water and the like. Moreover, the obtained cellulose can be subjected to various processings or treatments according to its applications. Such processings or treatments may be properly performed by those skilled in the art.

It can be confirmed that the recovered insoluble polysaccharide is cellulose, by chemical analysis or instrumental analysis known to those skilled in the art. For example, the insoluble polysaccharide can be confirmed to consist of D-glucose by constituent sugar analysis, such as alditol acetate method. Further, each glucose unit can be confirmed to be type β (that is, each three-dimensional configuration between glucose units is type β) according to an absorbance at 890 cm$^{-1}$ by infrared rays absorption analysis (IR). Furthermore, in constituent sugar analysis using sodium borodeuteride (NaBD$_4$) as a reducing agent after complete methylation, each linking pattern between glucose units is confirmed to be (1→4) linking. This can also be confirmed by other methods, such as Smith degradation. Chemical analysis and instrumental analysis as described above are routinely employed in the art, thus they can be appropriately performed by those skilled in the art.

The molecular weight of cellulose according to the invention can be measured using methods known to those skilled in the art, including gel chromatography using gel filtration, gel permeation chromatography (GPC), and the like. Gel used for gel filtration is not specifically limited, because those skilled in the art can select a proper gel. A preferred gel is TSKgel HW-65F. Thus determined molecular weight of cellulose according to the invention is not specifically limited. A preferred molecular weight of the cellulose ranges from 350,000 to 800,000, more preferably 500,000 to 700,000, and the most preferably about 600,000. The resultant average molecular weight (Mw) is preferably 550,000 to 600,000, more preferably about 575,000.

The crystal structure of the cellulose of the invention can be determined by X-ray diffraction. Process for X-ray diffraction is not specifically limited. For example, insoluble polysaccharide (cellulose of the invention) obtained as described above is put into a plastic container with a flat and smooth surfaced bottom, and freeze-dried to prepare a film with a smooth surface (1 mm of thickness, 14 mm×14 mm). X-ray diffraction analysis can be performed by irradiating X-rays over this smooth surface. When cellulose is analyzed by this concrete technique, the cellulose of the invention shows no peak at 2θ=5.0° to 45.0°. That is, the cellulose of the invention has no definite crystal structure.

In the above constituent sugar analysis, when treated with 2M trifluoroacetic acid for 2 hours at 121° C., the cellulose of the invention is completely hydrolyzed to glucose, but known vegetable celluloses resist against such hydrolysis and are not completely hydrolyzed. Further, in X-ray diffraction as described above, the cellulose of the invention shows no peak at 2θ=5.0° to 45.0°, but the known vegetable celluloses show peaks at 2θ=14.6°, 16.5° and 22.7°. This suggests that the cellulose of the invention has no definite crystal structure while the known vegetable celluloses have a crystal structure identical to understandings obtained so far. Therefore, the cellulose of the invention is totally different from known celluloses.

Accordingly, the present invention relates to cellulose having the physico-chemical properties of:
 (a) being completely hydrolyzed when it is treated in 2M triflubroacetic acid for 2 hours at 121° C.; and
 (b) showing no peak at 2θ=5.0° to 45.0° when it is lyophilized (freeze-dried) and subjected to X-ray diffraction analysis.

The molecular weight of the cellulose, which is not specifically limited is preferably 350,000 to 800,000, more preferably 500,000 to 700,000, and the most preferably about 600,000. The molecular weight is determined by dissolving 1 mg of insoluble polysaccharide obtained as described above in 0.5 ml of cadoxen (tris(ethylendiamine) cadmium hydroxide), subjected to gel chromatography (TSKgel HW-65F, 15 cm×0.5 cm), fractionated every 2 minutes (flow rate: 0.3 ml/minute), then analyzing the sugar content of each fraction by the phenol-sulfuric acid method. The resultant average molecular weight (Mw) is preferably 550,000 to 600,000, more preferably about 575,000.

INDUSTRIAL APPLICABILITY

The present invention provides technology to produce cellulose from filamentous fungi. Further, the present invention provides novel cellulose, which is produced by filamentous fungi and can be utilized as various industrial materials, additives, and the like.

EXAMPLES

The present invention is further described in the following examples. These examples are provided for illustrative purposes only, and are not intended to limit the scope of the invention.

Example 1

Culture of *Microdochium nivale* and Recovery of Insoluble Polysaccharide 0.06 g of *Microdochium nivale* (FERM BP-7298) was inoculated in 200 ml of a potato dextrose (2.4%) liquid medium (pH 5.1) (manufactured by Difco) and cultured while turning the medium placed in a 500 ml flask at 200 rpm. The culture medium was centrifuged (15,000×g, 20 minutes) to collect jelly-like substances in the upper layer of the precipitated cells. The collected substances were washed with distilled water to obtain insoluble polysaccharide.

The productivity of the insoluble polysaccharide was examined in the above culturing process by varying the culture temperature in the range of 4° C. to 20° C.

In FIG. 1B showing the results of this examination, each value represents a dry weight per litter of the culture medium at a point when the maximum amount of extracellular insoluble polysaccharide was produced at each temperature (4° C. : on day 14, 10° C.: on day 14, 15° C.: on day 4, 20° C.: on day 6). The symbol, "●" indicates the amount of insoluble polysaccharide and "■" indicates the amount of filamentous fungus. The highest productivity was seen in the culturing at 4° C. according to FIG. 1B.

Next, changes with time in the amount of insoluble polysaccharide produced in case of culturing *Microdochium nivale* at 4° C. were examined. FIG. 1A shows the results of this examination. The symbol "●" indicates the amount of insoluble polysaccharide and "■" indicates the amount of filamentous fungus in FIG. 1A. Insoluble polysaccharide produced in the culture fluid continued to increase until day 14 then it started to decrease according to FIG. 1A.

Based on these results, 0.06 g of *Microdochium nivale* was cultured for 14 days at 4° C. Thus, insoluble polysaccharide, 4 g per liter of the culture medium, was obtained.

Example 2

Identification of Insoluble Polysaccharide Produced by *Microdochium nivale*.

(1) Constituent Sugar Analysis 0.5 ml of 2M trifluoroacetic acid was added to 1 mg of insoluble polysaccharide obtained in Example 1, then the mixture was hydrolyzed for 3 hours at 121° C. Trifluoroacetic acid was removed from the mixture using nitrogen gas. The resulting monosaccharide was reduced with sodium borohydride. The hydroxyl groups of the reduced monosaccharide were acetylated by Merkle and Poppe's method (Merkle and Poppe, Methods Enzymol. 230, 1–15, 1994). Analysis with gas chromatography (column; Spelco SP-2330: internal diameter 0.25 mm×length 15 m, temperature condition; kept at 170° C. for 4 minutes: elevated from 170° C. to 240° C. at a rate of 8° C./minute: kept at 240° C. for 8 minutes) resulted in a peak only for acethylated glucose. Therefore the insoluble polysaccharide was confirmed to be polyglucan (FIG. 2).

Figure 3:
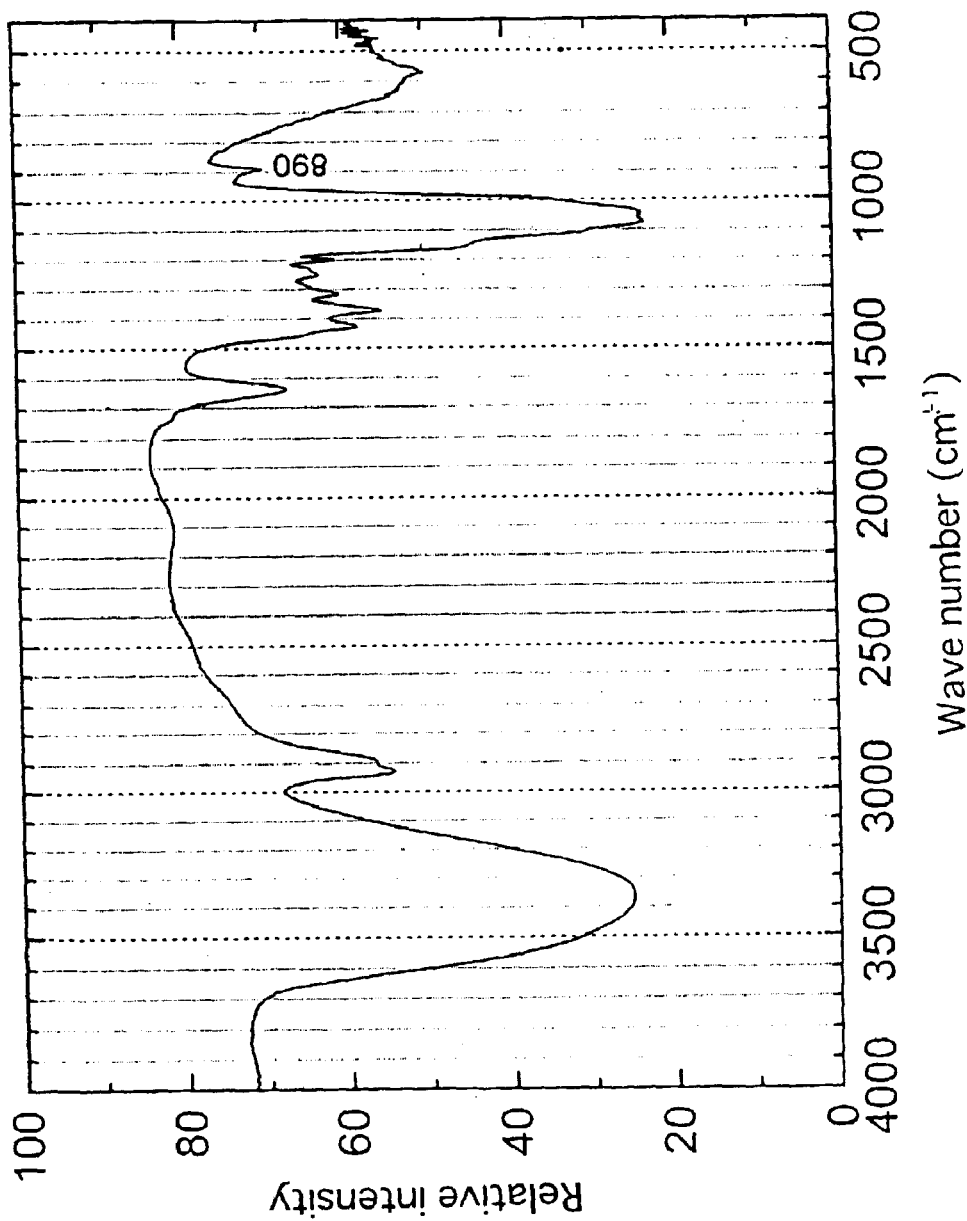
FIG. 3 shows the results of FT-IR analysis on insoluble polysaccharide produced by *Microdochium nivale*.

(2) Determination of Three-Dimentional Configuration for Carbon at Position 1 in Glucose The insoluble polysaccharide obtained in Example 1 was freeze-dried, and then ground down together with potassium bromide and shaped into tablets. Subsequently the three-dimentional configuration of carbon at position 1 in the glucose was examined by Fourier transform infrared rays absorption analysis (FT-IR). As a result, a peak was detected at 890 cm$^{-1}$, suggesting that this was type β (FIG. 3).

(3) Determination of the Linking Pattern Between Glucose Units

To examine the linking position of glucose in the insoluble polysaccharide obtained in Example 1, hydroxyl groups existing in the insoluble polysaccharide were completely methylated, and subjected to constituent sugar analysis as described in (1) except that sodium borodeuteride (NaBD$_4$) was used for reduction.

The complete methylation was performed as follows. First, 10 ml of dimethyl sulfoxide (DMSO) was added to 80 mg of insoluble polysaccharide, then the mixture was stirred in a flask with argon gas sealed therein for 2 hours, followed by ultrasonication for 2 hours. The insoluble polysaccharide dissolved partially. To completely dissolve the insoluble polysaccharide, an additional 15 ml of DMSO and 9 ml of sodium dimsyl (The sodium dimsyl had been prepared by adding 10 ml of DMSO to 0.5 g of oleaginous sodium hydride in a flask containing argon gas sealed therein) were added to the mixture, then stirred for 2 minutes followed by ultrasonication for 2 minutes. Then 1 ml of methyl iodide was added to the mixture in ice and dialyzed against distilled water.

Figure 4:
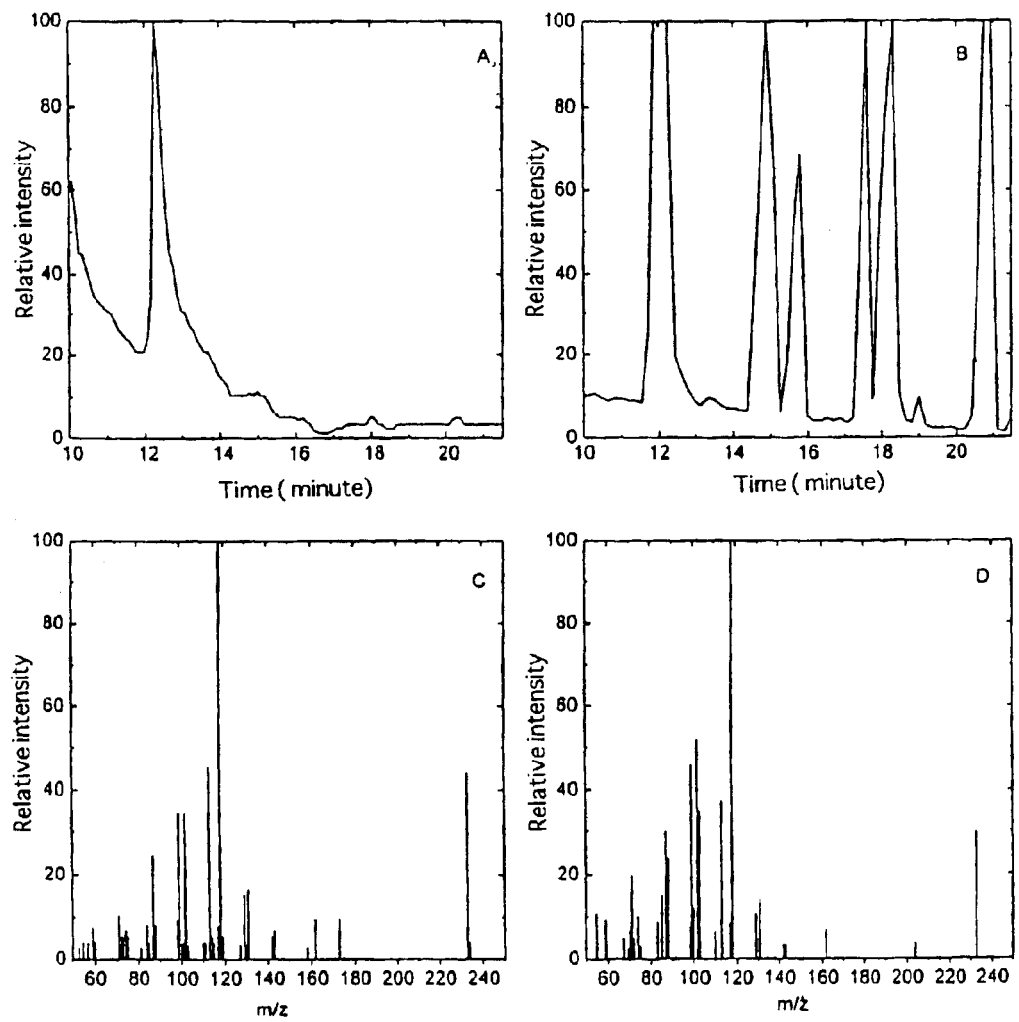
FIG. 4 shows the analytical results of the linking pattern between glucose units in the insoluble polysaccharide produced by *Microdochium nivale*.

Thus obtained products were analyzed with a gas chromatography mass spectrometer (GC/MS) (Column: SpelcoSP-2330, Internal diameter 0.25 mm×Length 15 m, Temperature condition: maintained for 4 minutes at 190° C.; elevated from 190 to 240° C. at a rate of 4° C./minute; maintained for 8 minutes at 240° C.). A control was prepared by similarly treating the standard sample of cellulose, whose 30% of hydroxyl groups had already been methylated. FIG. 4 shows the results. In FIG. 4, "A" indicates the gas chromatogram of the insoluble polysaccharide; "C" indicates the mass spectrum of substances eluted at about 12 minutes of the gas chromatogram of "A"; "B" indicates the gas chromatogram of 30% methylated cellulose; and D indicates the mass spectrum of substances eluted at about 12 minutes in the gas chromatogram of "C." As shown in FIG. 4, for the insoluble polysaccharide, only glucose whose carbons at positions 2, 3 and 6 had been methylated was detected.

(4) Conclusion

The results obtained in (1) to (3) above suggest that the insoluble polysaccharide consisted only of cellulose, which is β-(1→4)-glucan.

Example 3

Figure 5:
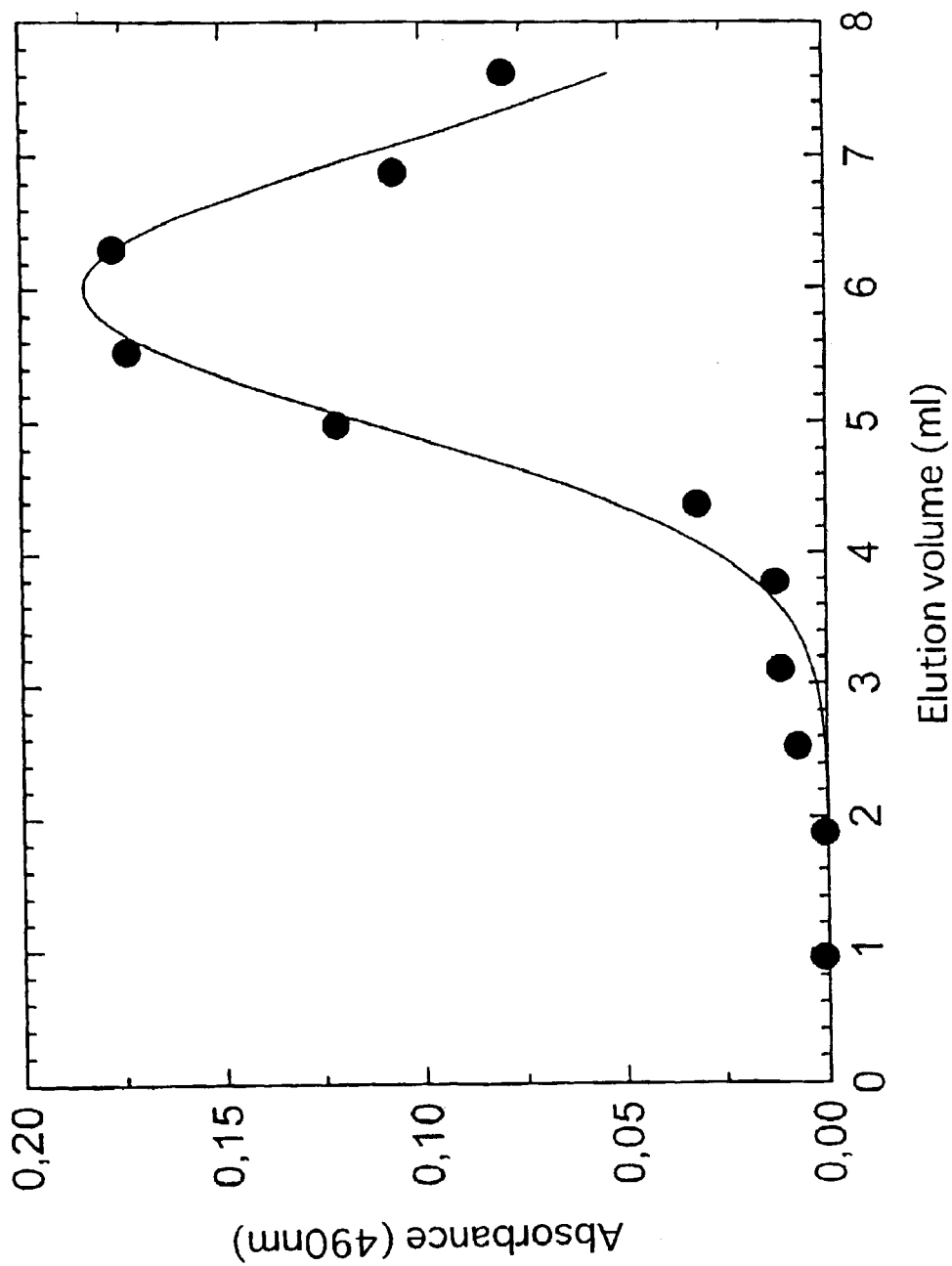
FIG. 5 shows the results of gel filtration chromatography performed on the insoluble polysaccharide produced by *Microdochium nivale*.

Molecular Size of Cellulose 1 mg of insoluble polysaccharide obtained in Example 1 was dissolved in 0.5 ml of cadoxen (tris(ethylendiamine)

cadmium hydroxide), subjected to gel chromatography (TSKgel HW-65F, 15 cm×0.5 cm), and then fractionated every 2 minutes (flow rate: 0.3 ml/minute). Analysis of the sugar content of each fraction by the phenol sulfuric acid method resulted in a single peak, as shown in FIG. 5. Molecular weight was measured using dextran (molecular weight: 12,000, 50,000 and 150,000) as a standard sample. The majority of the insoluble polysaccharide had molecular weight of 600,000. The average molecular weight (Mw: weight average molecular weight) was 575,000.

Example 4

Crystal Structure Analysis

The insoluble polysaccharide obtained in Example 1 was put into a plastic container with a flat and smooth bottom and freeze-dried to prepare a film with a smooth surface (1 mm of thickness, 7 mm×7 mm). Then X-ray diffraction analysis was performed by irradiating X-ray over the smooth surface. This analysis resulted in no definite peak. On the other hand, X-ray diffraction analysis made for a filter paper (Whatman) as a control resulted in peaks at $2\theta=14.6°$, $16.5°$, and $22.7°$, which is specifically observed for the three-dimensional structure of vegetable celluloses. Therefore, it was shown that unlike known vegetable celluloses, the insoluble polysaccharide has no definite crystal structure.

All publications, patents and patent applications cited herein are incorporated herein by reference in their entirety.

What is claimed is:

1. A method of producing cellulose comprising the steps of:
    (i) culturing filamentous fungus belonging to the genus Microdochium and having the ability to produce cellulose; and
    (ii) recovering cellulose from a culture obtained by the step (i).

2. The method according to claim 1 wherein the filamentous fungus is a *Microdochium nivale*.

3. The method according to claim 1 wherein the filamentous fungus is *Microdochium nivale* deposited as FERM BP-7298.

* * * * *

UNITED STATES PATENT AND TRADEMARK OFFICE
CERTIFICATE OF CORRECTION

| | | |
|---|---|---|
| PATENT NO. | : 6,958,227 B2 | Page 1 of 1 |
| APPLICATION NO. | : 10/369327 | |
| DATED | : October 25, 2005 | |
| INVENTOR(S) | : Naoki Morita | |

It is certified that error appears in the above-identified patent and that said Letters Patent is hereby corrected as shown below:

Title page,
Item [73], Assignee,
Insert --Secretary of Agency of Industrial Science and Technology, Tokyo (JP)-- before "Incorporated Administrative Agency National Agriculture and Bio-Oriented Research Organization, Ibaraki (JP)".

Signed and Sealed this

Fifth Day of January, 2010

David J. Kappos
*Director of the United States Patent and Trademark Office*